United States Patent [19]

Beck et al.

[11] Patent Number: 4,585,522

[45] Date of Patent: Apr. 29, 1986

[54] AUTOMATICALLY FED DISTILLATION STILL

[75] Inventors: Boyd R. Beck, Spring City, Utah; LaMar H. Stewart, Gunnison, Utah 84634; Steven L. Tapp, Ephraim, Utah; Don L. Anderson, Jr., Gunnison, Utah; Daniel E. Nuffer, Ephraim, Utah

[73] Assignee: Lamar H. Stewart, Gunnison, Utah

[21] Appl. No.: 319,453

[22] Filed: Nov. 9, 1981

Related U.S. Application Data

[63] Continuation-in-part of Ser. No. 134,878, Mar. 28, 1980, Pat. No. 4,314,890.

[51] Int. Cl.⁴ .............................................. B01D 3/02
[52] U.S. Cl. ..................................... 202/181; 202/206; 202/233; 202/234; 202/235; 203/DIG. 13
[58] Field of Search ................ 202/181, 206, 233-235; 203/DIG. 13, 1, 2, 19

[56] References Cited

U.S. PATENT DOCUMENTS

| 102,633 | 5/1870 | Wheeler et al. | 202/234 |
| 2,902,028 | 9/1959 | Manly | 202/234 |
| 3,325,376 | 6/1967 | Eckert | 202/234 |
| 3,330,740 | 7/1967 | Deffy | 202/181 |
| 3,364,731 | 1/1968 | Hook | 202/206 |

*Primary Examiner*—Frank Sever
*Attorney, Agent, or Firm*—Thorpe, North & Western

[57] ABSTRACT

Heated distillation still for separating ethanol-water mixtures divided into an upper solar absorbent vaporization section and a lower pre-heating section by a vaporization floor, float means to automatically control the ethanol-water feed to the lower portion of the pre-heating section when distillation is taking place, means to evenly distribute the ethanol-water mixture on the vaporization floor, means to heat the ethanol-water mixture in the distillation chamber, and means to remove or recycle residual aqueous liquid from the lower end of the vaporization section.

6 Claims, 5 Drawing Figures

AUTOMATICALLY FED DISTILLATION STILL

BACKGROUND OF THE INVENTION

This invention is a continuation in part of our earlier application, Ser. No. 134,878, filed Mar. 28, 1980, now U.S. Pat. No. 4,314,890.

This invention relates to a system and method for the distillation of ethanol from ethanol-water mixtures through the use of solar, electrical, or other energy sources. More particularly, this invention relates to a system and method for the separation of ethanol from ethanol-water mixtures wherein the feed to the distillation device is automatically controlled so as to feed water-ethanol mixtures to the distillation chamber only when the chamber is sufficiently hot to allow distillation to take place.

The distillation of ethanol from ethanol-water mixtures is well known for the recovery of ethanol for alcoholic beverages and for industrial purposes. However, with the recently spiraling costs of fossil-based fuels, the utilization of ethanol in internal combustion engines has become increasingly important. Ethanol may be prepared naturally by fermentation and may also be prepared by industrial processes such as the hydration of ethylene. In both methods of manufacture, a dilute aqueous solution of ethanol is formed requiring the ethanol to be removed from the greater portion of the water in order for it to function effectively as a fuel in an internal-combustion engine. In our earlier patent application, Ser. No. 083,281, an apparatus and method for removing ethanol from ethanol-water mixtures was disclosed wherein the ethanol-water mixtures were preheated by solar means and were then passed to a solar vaporization chamber wherein the ethanol was distilled or vaporized from the water utilizing solar energy as the sole source of heat.

While the above-mentioned invention provides an extremely improved method for the utilization of solar energy, there are many times when such energy is not readily available. Moreover, there are times when the combined utilization of solar and other forms of energy might operate more economically when other factors are taken into consideration.

OBJECTS AND SUMMARY OF THE INVENTION

It is therefore an object of the present invention to provide an efficient distillation still for the separation of water-ethanol mixtures by solar, electrical, or other forms of energy, or a combination of such forms of energy.

It is also an object of the present invention to provide a still for the separation of water-ethanol mixtures wherein the feed to the vaporization apparatus is controlled by the temperature of the water-ethanol mixture and rate of distillation within the vaporization chamber.

It is further an object of the present invention to provide a distillation still for the separation of water-ethanol mixtures wherein the mixture to be separated is preheated in a chamber immediately adjacent to the vaporization chamber wherein the same source or sources of energy are used to both preheat and vaporize the mixture and is also used to control the rate at which water-ethanol mixture is fed through the preheating chamber.

These and other objects are accomplished by means of an inclined still, heated by solar, electrical, or other forms of energy, or a combination of such forms of energy. The inclined still comprises a lower preheating chamber and an upper vaporization chamber having a vaporization floor. The vaporization floor thus serves as the dividing barrier between the lower preheating chamber and the upper vaporization chamber. Water-ethanol mixtures entering the preheating chamber are heated by an appropriate energy source, such as by solar energy striking the vaporization floor, or by electrical resistance heaters that are adjacent the vaporization chamber. As the water-ethanol mixture is heated in the preheating chamber, the specific gravity of the mixture becomes less dense allowing the mixture to expand and eventually boil causing the mixture to rise to the top of the preheating section and spill over onto the vaporization floor. In the vaporization chamber, the ethanol is separated from the aqueous solution and may be passed into a fractionation column, or equivalent device. The residual liquid at the bottom of the vaporization chamber is removed and disposed of or recycled back to the preheating chamber depending upon the ethanol content of such residual liquid.

The feed of water-ethanol to the still is controlled by the temperature of the water-ethanol mixture in the apparatus and the rate of ethanol distillation. The water-ethanol feed is controlled by a float valve such that when the still is not working the liquid level within the feed container housing the float valve and the liquid level within the still are the same. As the still is heated and the water-ethanol mixture within the preheating action expands and begins to vaporize or be distilled, the level of the water-ethanol mixture in the feed chamber is lowered and the float valve opens permitting additional feed to enter into the feed chamber. However, the feed entering into the feed chamber through the float valve is controlled by the rate at which the ethanol is removed from the ethanol-water mixture within the still.

DRAWINGS OF THE INVENTION

The above and other objects, features, and advantages of the present invention will be more apparent from the following more particular description, presented in connection with the following drawings, in which.

DETAILED DESCRIPTION OF THE INVENTION

Figure 1:
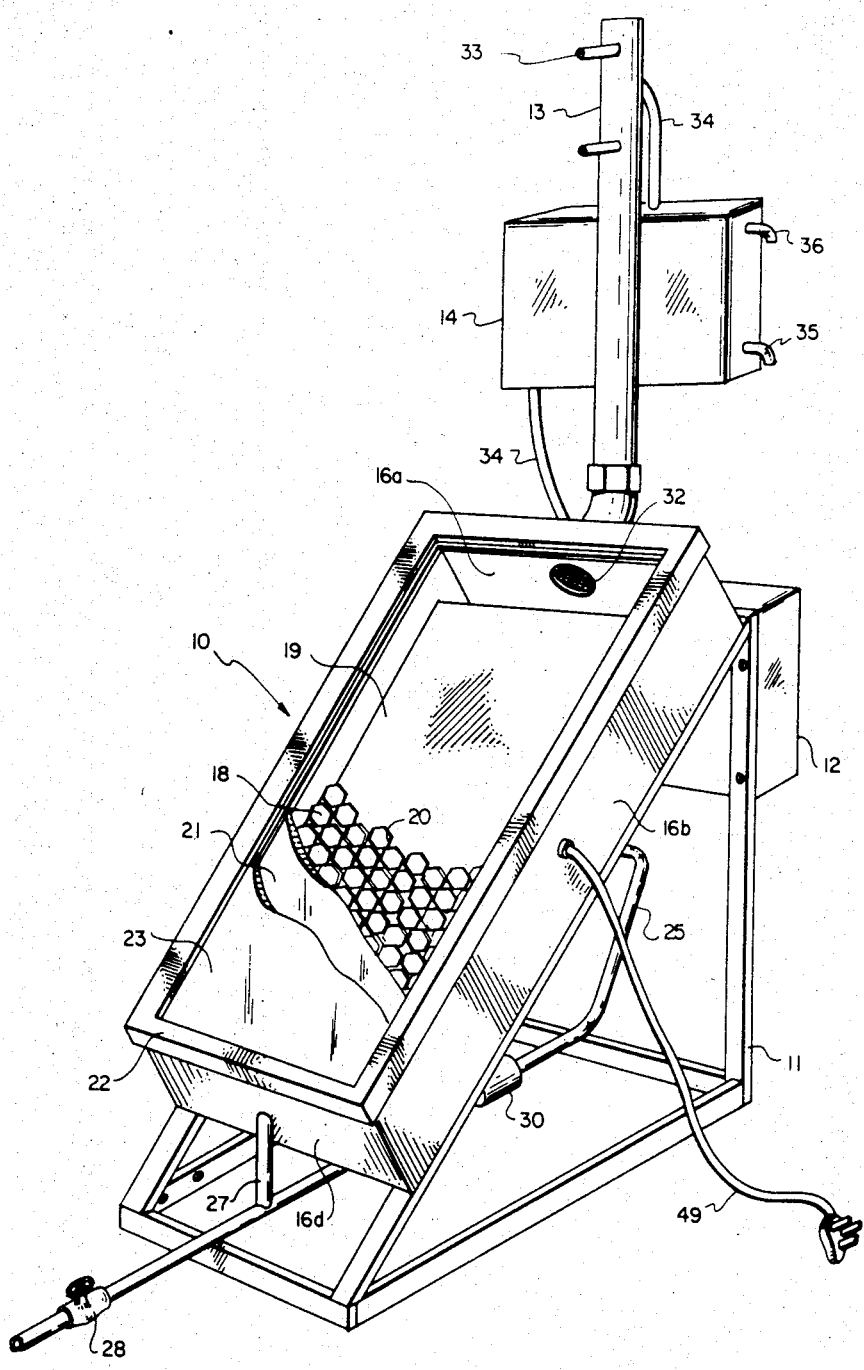
FIG. 1 is a front perspective view of the preferred embodiment of the invention partially broken away in order to illustrate the vaporization section of the apparatus.
Figure 2:
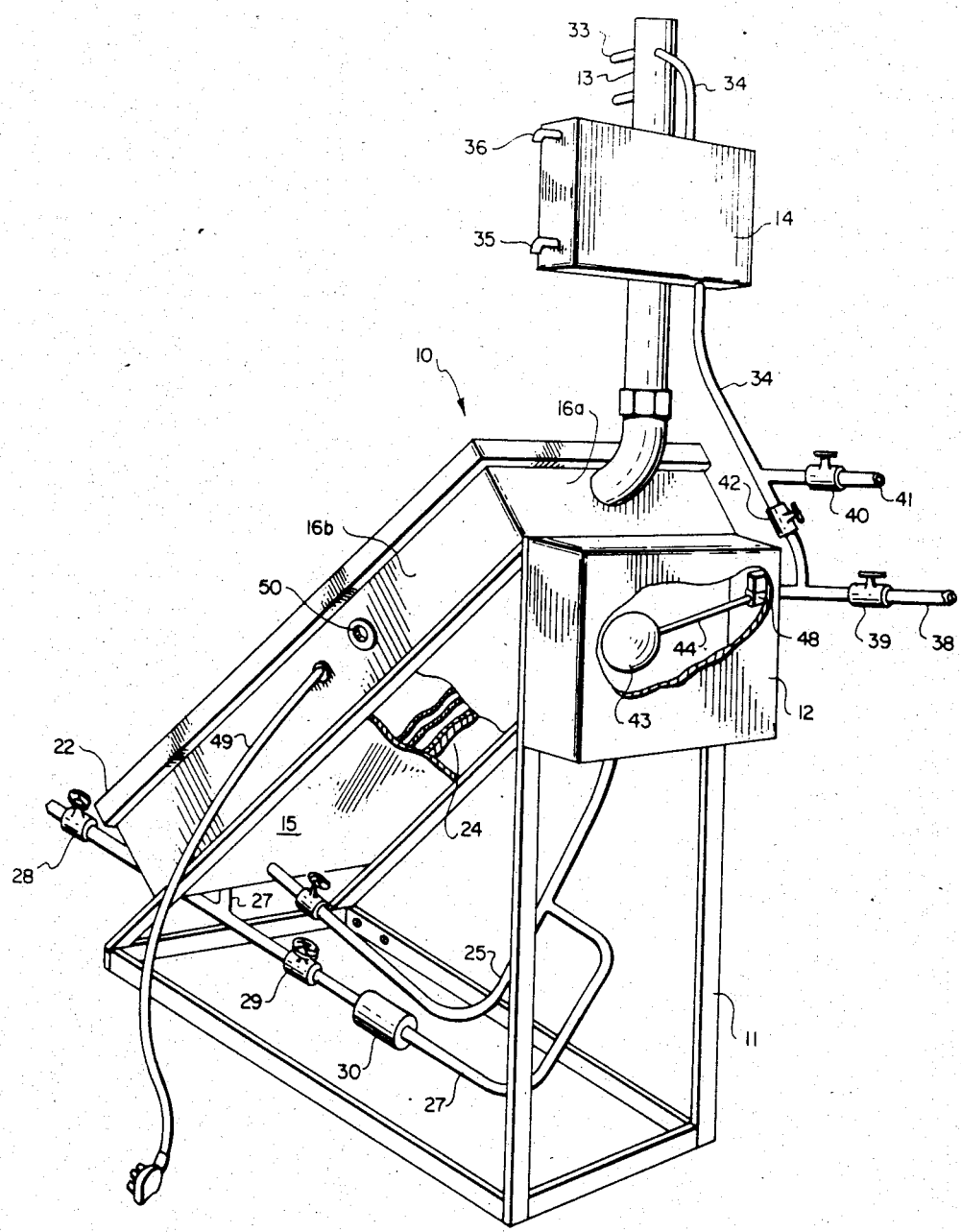
FIG. 2 is a rear elevational view of the apparatus shown in FIG. 1 partially broken away to show the preheating chamber of the apparatus and the float valve of the feed chamber.
Figure 3:
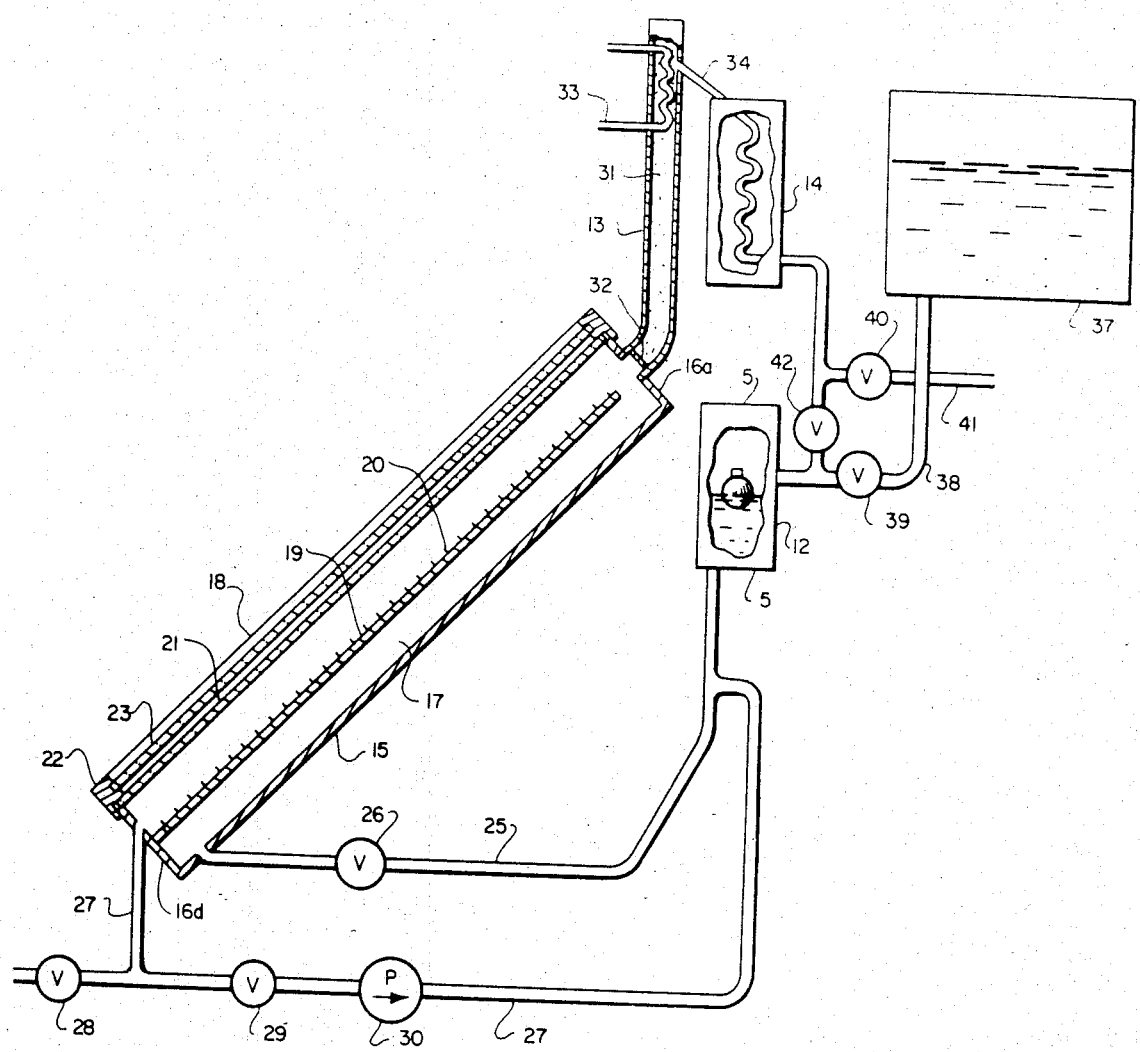
FIG. 3 is a side cross-sectional view of the apparatus shown in FIG. 1 taken along line 3—3 thereof and also contains a schematic flow diagram showing the operation of the apparatus.
Figure 4:
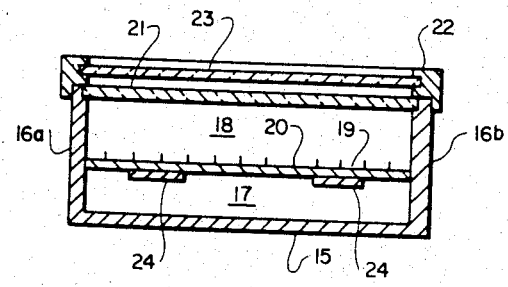
FIG. 4 is a transverse cross-sectional view of the apparatus shown in FIG. 1 taken along line 4—4 thereof.
Figure 5:
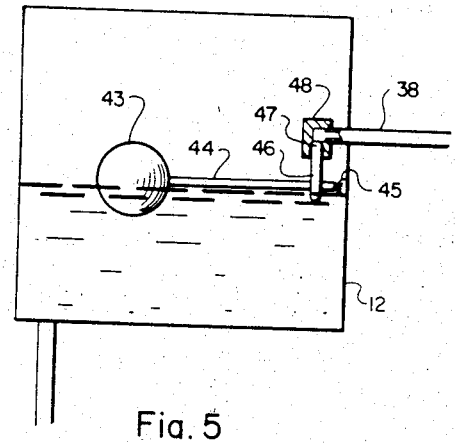
FIG. 5 is a cross-sectional view of the feed chamber showing one type of level control float and valve arrangement taken along lines 5—5 of FIG. 3.

There is shown in FIGS. 1 through 5 a complete and preferred embodiment of the invention. While the invention herein disclosed is concerned only with a distillation still 10 and related support structure, a fractionation column 13 is also shown in the drawings to give an indication of how the still could be used in a complete distillation and fractionation system. Further, while water-ethanol mixtures from various sources may be utilized in this invention, the apparatus will be described in terms of the separation of the water-ethanol mixture containing about 9 to 13% ethanol. This is representative of water-ethanol mixtures obtained by the natural fermentation of carbohydrate sources.

The apparatus as shown consists of an inclined still 10 supported by stand 11. A feed chamber 12 is connected to the rear of the still 10. A fractionation column 13 and condenser 14 may be connected to and located above the apparatus as shown.

The still 10 is generally rectangular in shape, having a generally flat insulated floor 15 surrounded on each side by insulated upwardly extending walls 16a, b, c and d. Dividing the still into a preheating chamber 17 and a vaporization chamber 18 is a vaporization floor 19. Floor 19 may be any suitable material. Preferably it is realized from materials that readily absorb heat from external sources; and, in turn, transfer at least a portion of this absorbed heat to the solution in the preheating chamber. For example, if solar rays are allowed to strike the upper surface of the floor 19 (e.g., through a translucent top or lid 22), the floor 19 may advantageously be a metal having a solar absorbent surface. Small heat absorbing projections 20, which inhibit the downward flow of water-ethanol solution, thereby allowing sufficient time for ethanol distillation from such solutions, are selectively placed on the upper surface of the floor 19. These projections 20 may consist of expanded metal sheets having a honeycomb or similar configuration placed over the vaporization floor 19. Such expanded metal sheets are commonly used in the construction industry as a base for plaster. This type of floor is a considerable improvement over the fabric type of material disclosed in Ser. No. 083,281 in that the floor does not become plugged by foreign matter but remains free of foreign matter since liquid flowing over the surface of the floor 19 washes these materials from this surface. Floor 19 is contiguous with lower end wall 16d and sidewalls 16b and 16c, but terminates short of upper end wall 16a to enable the water-ethanol from the preheating chamber 17 to spill over the upper end of vaporization floor 19 onto the upper projections 20. It follows that the upper end of floor 19 must be horizontally level so that the water-ethanol mixture will be uniformly distributed onto the surface of floor 19. The actual distance between the upper end of floor 19 and end wall 16a is not critical as long as there is sufficient room for removal of distilled vapors from both chambers 17 and 18 of the still 10 into a fractionation column 13, or similar collection and/or purification device.

In one embodiment, the still 10 may contain one or more transparent or translucent covers which are capable of transmitting solar energy. Depending upon the climatic conditions, two or more such layers could be used. The primary cover 21 is preferably sealed into walls 16 by appropriate means such as gaskets, caulking and the like. A lid 22 containing one or more layers of glass or plastic 23 may be placed about the upper edges of walls 16 and over cover 21. Each layer of covering, i.e., layers 21 and 23, is separated from each other by a dead-air space. When constructed in this manner the transmission of light through the cover is not inhibited but the outward loss of heat within the vaporization chamber is effectively prevented. Moreover, cover 21 remains heated thereby helping prevent the collection of condensed vapors thereon as is done in conventional solar stills.

Alternatively, the cover 21, especially the underneath side thereof, could be realized using an opaque, or nearly opaque, solar absorbing material. The heat thus absorbed, would not only prevent the collection of condensed vapors on the underside of the cover 21, but would also serve to further heat the vaporization chamber 18.

Floor 15, the lower end wall 16d and sidewalls 16b and 16c are insulated to retain heat. Any form of insulation conventionally used which will provide an R-15 to R-30 rating is adequate. Typical of such insulating materials are urethane and polystyrene foams. The upper wall 16a is also preferably insulated but need not be.

Attached to the underside of vaporization floor 19 and running essentially the length thereof may be one or more electrical resistance heaters 24 which are positioned so as to heat liquid contained in preheating chamber 18 and also heat the surface of vaporization floor 19.

Sources of energy other than solar energy may be used, of course, to heat the preheating chamber 17 and the vaporization chamber 18. As indicated in the preceding paragraph, electrical heating coils could be imbedded into or attached to the floor 19 and surrounding walls. Steam derived from either a geothermal source or from natural gas, coal, or similar fuels, could also be selectively distributed throughout the floor 19 and/or surrounding walls in appropriate tubing. Such tubing could even be selectively positioned on the upper surface of the floor 19 so as to serve as the portions 20 that are used to inhibit the downward flow of the water-ethanol solution. Other forms of energy, both known and yet to be discovered, could also be used to perform the necessary heating function by those skilled in the art.

A line 25 closeable by valve 26 interconnects feed chamber 12 with the lower portion of preheating chamber 17. A drain or recycle line 27, whose flow direction is controlled by drain valve 28 or recycle valve 29 and pump 30, completes the plumbing of the still 10.

As mentioned, a fractionation column 13 may be interconnected with still 10 via an aperture in upper end wall 16a. Any suitable type of fractionation column may be used. Glass beads, glass wool or any other conventional packing material 31 is commonly used in fractionation columns. A retaining screen 32 or glass wool plug prevents the packing material from entering the still 10 while allowing vapors from the still to enter the column. The walls of column 13 are insulated in essentially the same manner as the walls of the still. Preferably, a coiled water line 33 is placed in the upper end of fractionation column 13 adjacent outlet line 34. Line 34 passes through condenser 14 which is essentially a water-cooled jacket having an inlet 35 and outlet 36.

The water-ethanol feed system formed by the still and fractionation column may have an optional water-ethanol storage tank 37 connected to feed chamber 12 via line 38 which may be closed by valve 39. Line 34 (from the fractionation column and passing through condenser 14) either interconnects line 38 when valve 40 is closed or ethanol product withdrawal line 41 when valve 42 is closed and valve 40 is open.

The flow of water-ethanol through the still is controlled by means of a float control valve located in feed chamber 12. Various valves can be used and thus the invention is not to be limited to the specific embodiment disclosed herein. Basically, the valve control consists of a float 43 attached to an arm 44 which is connected to a wall of feed chamber 12 via a swivel 45. A valve stem 46 interconnects the arm 44 a short distance away from swivel 45. A hydraulic valve head 47 adapted to seat in fluid tight relationship into valve chamber 48 completes the feed system. The feed chamber 12 is positioned relative to still 10 such that the level of liquid in the preheating chamber 17 of the still will be just below the upper end of vaporization floor 19 when the level of liquid in the feed chamber raises the float 43 high enough to seat valve head 47 into the valve body 48, thereby closing off line 38.

With the distillation still and system described above, the specific mode of operation will now be disclosed.

A water-ethanol mixture prepared synthetically or by fermentation is stored in tank 37. When valves 39 and 26 are opened, feed chamber 12 and preheating chamber 17 are filled by means of fluid flow via lines 38 and 25. As the water-ethanol mixture approaches the top of vaporization floor 19 in chamber 17, feed chamber 12 also fills causing float 43 to rise, which rising thrusts valve head 47 into the valve body 48 and shuts off the fluid flow by hydraulic pressure.

As previously taught, still 10 may be heated by solar heat, electrically supplied heat, or a wide variety of other sources of heat, or a combination of such sources of heat. If solar heat is used, the positioning of the still relative to the sun, as taught in Ser. No. 083,281, may be applied to the present invention. Electrical energy, when used, is supplied to resistance heaters 24 via electrical line 49. A thermostat 50 may be used to control the flow of current to the heaters to provide the desired temperature within the still and allow for optimum usage of solar energy. If other sources of energy are used, suitable controls would likewise be employed to achieve the desired temperature.

As the temperature within the still rises, the water-ethanol mixture in preheating chamber expands and eventually boils, causing the solution to overflow onto the upper surface of vaporization floor 19. The barriers 20 delay the downward flow of the water-ethanol mixture along this floor 19.

The distillation process begins in the preheating chamber 17 and is intensified in vaporization chamber 18. The liquid passing downward along floor 19 becomes progressively more ethanol depleted as it approaches the lower end of chamber 18. Therefore, the liquid reaching the end of chamber 18 consists primarily of water with only minor amounts of ethanol. This ethanol depleted water is withdrawn via line 27 through valve 28 and is discarded. However, if the ethanol content is sufficiently high, valve 28 may be closed and valve 29 opened allowing the liquid to be recycled by pump 30 back to line 25. If desired, a hydrometric valve or equivalent may be used to determine the ethanol content of solution in line 27 and automatically effect a recycle if the ethanol content is sufficiently high. On the other hand, periodic analysis may be made of this residual solution by a hydrometer or a gas chromatograph or other conventional means in order to determine whether to recycle or discard the residual solution.

As the solution within chamber 17 spills over onto the floor of chamber 18, the water-ethanol within feed chamber 12 feeds by gravity flow into chamber 17. This causes the float 43 to lower, thereby unseating valve head 47 and allowing fresh feed from tank 37 to enter the feed chamber. As long as the temperature in still 10 remains sufficient to sustain distillation, the feed will be continuous. However, once the temperature in the still drops, the liquid level within chamber 17 automatically lowers, causing the valve head to seal off the flow of feed to feed chamber 12. Thus, water-ethanol mixture cannot flow through the still in the absence of adequate distillation temperatures. Moreover, the still operates automatically with few moving parts, thereby lessening the need of having an operator constantly monitoring the still.

As the temperatures within the vaporization chamber 18 become operational, the insulated cover 21 becomes sufficiently warm that ethanol vapors do not condense on the underside thereof. Therefore, essentially all of the vapors within both chambers of the still rise upwardly and may be withdrawn into a suitable container or further purifying element, such as the fractionation column 13. These vapors, depending upon the temperature within the still, consist primarily of ethanol with varying amounts of water.

The Column 13 functions to separate the lower boiling ethanol from the higher boiling water through a series of redistillations as commonly occurs in any fractionation column with the higher purity ethanol vapors passing to the upper portion of column 13 and through line 34 into condenser 14. Surprisingly, it has been found that the vapors entering the column can be fractionated to produce a high quality ethanol with a column which is shorter and less densely packed than is required with a conventional reflux fractional distillation system. A coiled water line 33 is preferably placed in the top of the fractionation column 13 to regulate the purity or concentration of ethanol vapors exiting line 34 and being condensed in condenser 14. The temperature of water flowing through line 33 is carefully regulated by means, now shown, to liquify vapors having too high a water concentration and prevent them from passing out of the column via line 34. In this manner the concentration of ethanol leaving the fractionation column can be controlled. For example, at 78.2° C. vapors exiting column 13 would contain 92% w ethanol whereas the condensed liquid would have 91% w or less ethanol. At 81.2° C. vapors exiting column 13 would contain 80% w ethanol whereas the condensed liquid would contain equal weights of water and ethanol. Through published tables, such as is contained on page 2117 of the Handbook of Chemistry and Physics, 39th Edition published by the Chemical Rubber Publishing Company, the optimum temperatures in coiled line 33 for a given ethanol concentration may be determined. The vapors condensed in column 13 are either redistilled in the column or pass downwardly into the still for redistillation.

The vapors passing through condenser 14 are liquified by heat exchange with cold water passing through the condenser via lines 35 and 36 and pass through valve 40 into line 41 for collection as fuel grade ethanol. If the temperature at the top of the fractionation column is not carefully controlled or if, for any other reason, the concentration of water in the ethanol is too high, valve 40 may be closed and valve 42 opened in order to recycle the condensate back to feed chamber 12. In the alternative, this product could be recycled directly to line 25 and bypass the feed chamber 12. If desired valves 40 and 42 could be replaced by a single hydrometric valve as disclosed in our earlier application, Ser. No. 083,231.

When operating the invention as described above, the temperatures within the still may vary somewhat. Preferably the temperatures will be between 80° and 95° C. in order to produce a fuel grade ethanol which is 160 proof or better. However, higher temperatures may be used for ethanol of lesser concentrations, or vice versa. It is also possible to utilize the system described herein to separate other liquids having different boiling points such as solvent-resin mixtures.

The following examples were carried out utilizing the system described above and are illustrative of the invention but are not to be considered as limitations thereof. For example, in certain examples a lower quality ethanol is produced due to the lack of temperature control in the fractionation column. Thus, a two-stage distillation is required to provide a higher grade of ethanol. It is apparent from the following examples that the invention may be utilized to produce various grades of ethanol and that a plurality of stills arranged in parallel or in series may be interconnected to obtain the grade of ethanol desired.

EXAMPLE I

The apparatus set up for this example included an inclined still 18×46 inches in size having a 3.5 gallon preheating chamber capacity. A tank containing an automatic float control valve was fed by gravity from a 50 gallon barrel, and the still was fed from the tank. A fractionation column 3 inches in diameter and 48 inches long was utilized which did not contain a temperature control coil at the top.

A 17.5 gallon sample of 24 proof alcohol from a mash fermentation process was placed in the barrel and fed to the tank and still. As the preheating chamber of the still filled to near capacity, the float control valve in the tank closed preventing the dilute alcohol from overflowing into the vaporization chamber of the still. The still and contents were at an ambient temperature of about 18.5° C. This example was conducted indoors without the use of solar energy. The still was equipped with electrical heating means.

The still was plugged into a 220 volt electrical outlet and a meter reading was taken. After 22 minutes, the temperature within the still had risen to 88.3°, and the water-ethanol solution in the preheating chamber began to boil. Six minutes later, the first drop of distilled ethanol was collected resulting in a start-up time of 28 minutes requiring an electrical consumption of 1.4 kilowatt hours. After start up, the distillation continued to produce one gallon of approximately 110 proof ethanol every 113.5 minutes requiring an energy consumption of 5.68 kilowatts per gallon. The waste water drained from the bottom of the vaporization chamber was analyzed periodically and averaged approximately 2% volume ethanol.

EXAMPLE II

The procedure followed in Example I was utilized except that the water-ethanol mixture was 10% ethanol, and the still operated to produce one gallon of 105 proof ethanol every 90 minutes with an energy consumption of 4.5 kilowatt hours per gallon. The wast water had an average ethanol content of 2.3% by volume.

EXAMPLE III

The 105 proof ethanol obtained from Example II was passed through the still a second time in order to provide a higher purity product. Following is a summation of the results obtained.

| | |
|---|---|
| Start up time | 27 minutes |
| Energy consumed in start up | 1.35 kw hr. |
| Gallons per hour of ethanol production | 1.25 gal/hr |
| Total volume of ethanol produced | 15,900 ml or 4.2 gal. |
| Average proof of ethanol produced | 150–155 proof |
| Total volume of waste water | 9,300 ml or 2.46 gal. |
| Average proof of waste water | 40 proof - 20% v ethanol |
| Kilowatt consumption per gallon of ethanol produced after start up | 2.66 kwh/gal. to 2.22 kwh/gal. |

EXAMPLE IV

A larger inclined still having a vaporization floor surface area of approximately two square meters was used in this example. The still was operated solely by electrical energy. The still was warm from a previous test and, therefore, required only an eight-minute warm up before condensate started collecting from the fractionation column. The still operated at an internal temperature of 94° C. The aqueous feed was controlled by a float valve and had an ethanol content of about 10% v. After start up, the still operated to produce about one gallon of 110 proof ethanol every 45.4 minutes utilizing 4.54 kilowatt hours of electricity per gallon. At the end of the run, the electricity was turned off and the float valve closed shutting off the flow of feed to the still.

EXAMPLE V

The still utilized in Example I is used in this example by modifying the upper portion of the fractionation column to include a constant temperature coil maintained by the circulation of water at a constant temperature of about 80.5° C.

The still is operated at 89.5° C. and is fed with 12% v dilute ethanol. After an initial start up of about 29 minutes, the still is automatically fed by use of a float control valve and produces about one gallon of 164 proof ethanol every three hours of operation leaving a waste product containing about 3% v ethanol. The average energy consumption is about 9 kilowatt hours per gallon.

What is claimed is:

1. An automatically fed distillation apparatus comprising:
    (a) an inclined still consisting of sidewalls, a lower endwall, an upper endwall, a bottom floor, and a top all being joined together to form a sealed still compartment, said compartment being divided into an upper vaporization chamber and a lower preheating chamber by a vaporization floor sealed to said sidewalls and lower endwall parallel to said bottom floor and top, said vaporization floor terminating at its upper end short of said upper endwall, thereby forming a baffle over which liquid from said preheating chamber may overflow into said vaporization chamber, means located on the top surface of said vaporization floor to impede the downward flow of liquid on said surface, means located in said preheating chamber for heating said vaporization floor and liquid contained in the preheating chamber to a specified temperature, inlet means for introducing liquid mixture feed into the lower end of said preheating chamber, outlet means for removing residual liquid from the lower end of said vaporization chamber, and outlet means in said upper endwall for removing vapors formed within the still compartment; and (b) feed control means interconnected with the inlet means to said preheating chamber for controlling the amount of liquid that flows thereinto, said feed control means consisting of a feed chamber having an inlet and an outlet and a hydraulically operated float control valve, which valve controls the flow of feed liquid through the feed chamber to the preheating chamber, said float control valve being selectively positioned in said feed chamber such that, when liquid in the preheating chamber is below a specified temperature, the valve will remain closed, and when liquid in the preheating chamber is raised to at least said specified temperature, the liquid in the preheating chamber expands in volume, thereby becoming less dense, and is pushed over the baffle end of the vaporization floor by the baffle end of the vaporization floor by the more dense, cooler liquid feed in the feed chamber that flows by gravity through the outlet of the feed chamber to the preheating chamber, the exiting of liquid feed from the feed chamber causing the float control valve to open, thereby allowing feed liquid to flow through the inlet to the feed chamber as long as the temperature of the feed liquid in the preheating chamber is above the specified temperature and the feed liquid is overflowing the baffle end of the vaporization floor.

2. A distillation apparatus as defined in claim 1 wherein said top of said inclined still comprises a translucent light transmitting top through which solar energy may pass.

3. A distillation apparatus as defined in claim 2 wherein said vaporization floor and means to impede the flow of liuids on the vaporization floor have solar absorbent surfaces.

4. A distillation apparatus as defined in claims 1 or 3 wherein said means for heating said vaporization floor comprises at least one electrical resistance heater element affixed thereto.

5. A distillation apparatus as defined in claim 1 wherein said top of said inclined still comprises a top that is at least partially opaque and that includes at least one solar absorbent surface.

6. A distillation apparatus as defined in claim 5 wherein at least one surface of said top is completely covered with a solar absorbent opaque material.

* * * * *